United States Patent

Cadot et al.

[11] Patent Number: 5,493,058
[45] Date of Patent: Feb. 20, 1996

[54] SYNTHESIS OF METHYL MERCAPTAN FROM DIMETHYL DISULPHIDE

[75] Inventors: Emmanuel Cadot, Paris; Michel Lacroix, Lyon; Annie Commarieu; Emmanuel Arretz, both of Pau, all of France

[73] Assignee: Elf Aquitaine Production, Courbevoie, France

[21] Appl. No.: 321,701

[22] Filed: Oct. 12, 1994

[30] Foreign Application Priority Data

Oct. 20, 1993 [FR] France .................... 93 12491

[51] Int. Cl.$^6$ .................... C07C 149/06
[52] U.S. Cl. .................... 568/70; 568/69
[58] Field of Search .................... 508/69, 70

[56] References Cited

U.S. PATENT DOCUMENTS

| 2,402,614 | 6/1946 | Farlow et al. | 568/70 |
| 3,336,386 | 8/1967 | Dovell et al. | 568/70 |
| 3,488,739 | 1/1970 | van Venrooy | 568/69 |
| 3,880,933 | 4/1975 | Kubicek | 568/70 |

FOREIGN PATENT DOCUMENTS

| 1386654 | 12/1964 | France | 568/70 |
| 2008331 | 1/1970 | France | 568/70 |
| 1903968 | 8/1970 | Germany | 568/70 |
| 1205537 | 9/1970 | United Kingdom | 568/70 |

*Primary Examiner*—James H. Reamer
*Attorney, Agent, or Firm*—Spencer & Frank

[57] ABSTRACT

The invention relates to the manufacture of methyl mercaptan by catalytic hydrogenation of dimethyl disulphide on a catalyst based on sulphide(s) of at least one transition metal.

The selectivity with respect to methyl mercaptan is considerably improved by working in the presence of water and/or hydrogen sulphide.

13 Claims, No Drawings

SYNTHESIS OF METHYL MERCAPTAN FROM DIMETHYL DISULPHIDE

FIELD OF THE INVENTION

The present invention relates to the field of mercaptans and its subject more specifically is a process for the selective preparation of methyl mercaptan from dimethyl disulphide (DMDS) by reaction with hydrogen on a catalyst consisting of transition metal sulphides.

BACKGROUND OF THE INVENTION

It is known that transition metal sulphides make it possible to perform hydrogenation reactions in the presence of large amounts of sulphur-containing molecules. Indeed, contrary to the standard hydrogenation catalysts, such as metals, the sulphide phases are not poisoned by sulphur-containing molecules. Their use for the catalytic reduction of aromatic disulphides to mercaptans is already described in the literature. Thus:

Patent Application NL 6,402,424 claims the use of metal sulphides, in particular platinum sulphide, for reducing diphenyl disulphide to phenyl mercaptan;

for this same reaction, Patents FR 2,008,331 and DE 1,903,968 recommend the metals Raney Ni or Raney Co, as well as the metals Ru, Rh, Pt, Ir and Pd or their sulphides;

according to Patent Application JP 56-81541, cobalt sulphide allows the reduction of aromatic compounds of the type $RS_nR'$ to mercaptans RSH and R'SH, R and R' being phenyl, p-nitrophenyl or 3,4-dichlorophenyl radicals.

If these processes are performed generally at relatively mild reaction temperatures (approx. 200° C.), the hydrogen pressures are, on the contrary, very high (50–100 bar) and catalyst/reactant ratios of the order of 2 are employed. In addition, the reaction is carried out in a closed reactor and in a three-phase medium: gas-liquid-solid.

The selective catalytic reduction of dimethyl disulphide to methyl mercaptan does not appear to have already been described. On the other hand, the total hydrogenolysis of dimethyl disulphide is widely used for the sulphuration of the hydrotreatment catalysts, which has become the most important industrial application of DMDS; in this case, DMDS is a hydrogen sulphide precursor which is the sulphuration agent of these catalysts. Work relating to the sulphuration of hydrotreatment catalysts using DMDS demonstrates that, during the presulphuration period of Co—Mo and of Ni—Mo catalysts, the distribution of the DMDS decomposition products (methyl mercaptan, dimethyl sulphide, hydrogen sulphide and methane) changes as a function of the temperature, a low temperature (of around 200° C.) favoring the formation of methyl mercaptan and that of dimethyl disulphide. On the other hand, at a higher temperature, hydrogenolysis of methyl mercaptan is rapid and leads to the predominant formation of hydrogen sulphide and methane.

Control of the hydrogenation of dimethyl disulphide in order to produce methyl mercaptan exclusively according to the reaction:

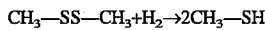

$$CH_3-SS-CH_3 + H_2 \rightarrow 2CH_3-SH$$

proves to be very difficult, given that these two compounds possess C-S bonds which are sensitive to hydrogenolysis, readily leading to the formation of hydrogen sulphide and methane. Furthermore, the additional formation of dimethyl sulphide, observed with catalysts based on transition metals (Co—Mo and Ni—Mo), is a factor which penalizes the production of methyl mercaptan.

Very large excesses of hydrogen, with respect to dimethyl disulphide, are used for the sulphuration of the hydrotreatment catalysts. By working with high proportions of hydrogen, the partial hydrogenation of DMDS limited to methyl mercaptan is disadvantaged with respect to a more complete hydrogenolysis of the sulphur-containing organic compounds.

However, by working with much lower hydrogen/DES ratios, side-reactions may occur on the catalyst and in particular favor formation of dimethyl sulphide by the reaction:

$$2\ CH_3SH \rightarrow CH_3SCH_3 + H_2S$$

DESCRIPTION OF THE INVENTION

The aim sought in the present invention consisted in finding a selective process for the manufacture of methyl mercaptan by catalytic hydrogenation of DMDS using relatively low amounts of hydrogen, in such a way as to facilitate the industrial exploitation of such a process in order to avoid extensive recycling of gas and to allow an efficient recovery of the methyl mercaptan, due to its specific physical properties (boiling point: +6° C. at atmospheric pressure).

The first works undertaken showed that transition metal sulphides do not perform the hydrogenation of dimethyl disulphide to methyl mercaptan selectively, even at temperatures in the region of or lower than 200° C., at a high or low proportion of hydrogen.

The research pursued with the aim of improving the selectivity towards methyl mercaptan led to the demonstration that the presence of water in the reaction between hydrogen and DMDS produces an unexpected effect on the catalytic properties of the catalysts, which is reflected in a spectacular increase in the selectivity towards methyl mercaptan. It has furthermore been observed that the presence of hydrogen sulphide in the reaction medium also provides a gain in selectivity towards methyl mercaptan; the effect of hydrogen sulphide is, however, less important than the effect produced by the water.

The subject of the present invention is thus a process for the manufacture of methyl mercaptan by catalytic hydrogenation of dimethyl disulphide on a catalyst based on sulphide(s) of at least one transition metal, characterized in that the process is performed in the presence of water and/or hydrogen sulphide.

The catalyst used according to the invention consists of a sulphide or a mixture of sulphides of at least one transition metal, this or these sulphide(s) being either in bulk form or incorporated with inorganic supports. The preferred transition metals are nickel, cobalt, molybdenum and/or tungsten. Inorganic supports which may be employed are the usual porous solids such as, for example, alumina, silica, silica-aluminas, zeolites or alternatively carbons.

In the supported catalysts, the weight content of transition metal may range from 0.1 to 50% and is preferably between 0.5 and 30%. The supported catalysts may be prepared by impregnation of the support using an aqueous solution of at least one metal derivative such as, for example, the nickel or cobalt nitrate, ammonium molybdate or ammonium tungstate. After impregnation, the solids are calcined at 400°–500° C. in air, except for those based on carbon, which are calcined under nitrogen. On conclusion of this treatment, the various transition metals are in the form of oxides. Their conversion to sulphide phases may be performed in a manner known per se, for example by subjecting the solids to the action of a mixture of hydrogen and dimethyl disulphide ($H_2$/DMDS molar ratio between 10 and 500) or of a mixture of hydrogen and hydrogen sulphide ($H_2$/$H_2S$ molar ratio between 1 and 500) at a temperature ranging from 150° to 500° C. The solids thus activated may be used either in extruded form or in powder form.

For a continuous production of methyl mercaptan, the process according to the invention is advantageously implemented in a tubular reactor in which the catalyst is arranged in a fixed bed or in a moving bed and into which the hydrogen and dimethyl disulphide reactants, as well as water or hydrogen sulphide, are introduced at controlled flow rates.

The process according to the invention may also be implemented in a stirred reactor. This mode of operation is suitable for discontinuous productions of methyl mercaptan.

The reaction may be carried out at atmospheric pressure or at pressures greater than atmospheric pressure (up to approximately 50 bar). The operating pressure depends, as a general rule, on the characteristics of the synthesis reactor and of the complementary elements defining the production installation, such as the hydrogen supply, the technique for recovery of the methyl mercaptan and the recycling of the gaseous effluents.

The actual reaction may take place within a fairly wide temperature range (50° to 400° C.), but in practice it is preferable to operate at a temperature between 100° and 250° C. so as to obtain methyl mercaptan with the highest selectivity.

The hydrogen/dimethyl disulphide molar ratio to be used is not less than 0.1 and may range up to 50. However, for reasons of industrial constraints, the hydrogen/DMDS ratio is usually between 0.5 and 10, and preferably between 0.8 and 4.

The proportion of water or of hydrogen sulphide to be introduced with the hydrogen and dimethyl disulphide reactants may range from 0.01 to 50% by weight relative to the dimethyl disulphide; it is preferably between 0.1% and 15%.

EXAMPLES

The examples which follow illustrate the invention without limiting it.

EXAMPLE 1

The hydrogenolysis tests on DMDS reported in this example, which demonstrates the effect of hydrogen sulphide and that of water on the selective formation of methyl mercaptan, were performed under conditions of low partial pressures of the reactants diluted in nitrogen.

a) Catalysts

The catalysts of commercial origin were prepared from the same activated alumina (specific surface: 256 $m^2.g^{-1}$; void volume: 0.6 $ml.g^{-1}$; content of impurities: 1,700 ppm). They were in extruded form and the metal constituents were in the form of oxides. The nature of the metal constituents and their proportions are given in the table which follows.

TABLE 1

| METAL CONSTITUENT | WEIGHT CONTENT (%) | CONCENTRATION ($10^{-4}$ mol/g cat.) |
| --- | --- | --- |
| Ni | 2.4 | 4.0 |
| Co | 2.4 | 4.0 |
| Mo | 9.3 | 9.7 |
| NiMo | Ki: 2.4 | 4.0 |
|  | Mo: 9.3 | 9.7 |
| NiW | Ki: 2.4 | 4.0 |
|  | W: 16.6 | 9.0 |
| CoMo | Co: 2.4 | 4.0 |
|  | Mo: 9.3 | 9.7 |

Sulphuration of the catalysts was carried out by treatment at 400° C. for 4 hours using a hydrogen sulphide/hydrogen mixture (containing 15 mol % of $H_2S$) at an hourly flow rate of 2 liters of mixture per gram of catalyst.

In order to simplify the description of the hydrogenation tests which follow, the sulphur-containing catalysts will now be identified in the tables simply by indicating the transition metal or metals, it being pointed out that masses of catalysts indicated are understood to refer to the total: metal sulphide(s)+$Al_2O_3$ support.

b) Hydrogenation of dimethyl disulphide

The tests were carried out at atmospheric pressure in a glass tubular reactor containing the ground catalyst in its central part. After having been purged with nitrogen, the reactor, housed in an electric oven, was brought to the reaction temperature. The reactants (hydrogen and DMDS), diluted in nitrogen, were subsequently introduced into the reactor with a total gas flow rate of 60 ml per minute. The partial pressure of DMDS was set at 2 kPa and that of hydrogen at 4 kPa, that is to say that the $H_2$/DMDS molar ratio was equal to 2. The reaction temperature was 200° C.

The gaseous effluents exiting the reactor were analysed directly by gas phase chromatography using a chromatograph whose injection valve was continuously supplied with the effluent. The catalysts of Table 1, as well as the alumina which served as a support for these various catalysts, were tested under the same conditions. The results reported in Table 2 give the relative selectivities in respect of methyl mercaptan (MESH) and of dimethyl sulphide (DMS) for tests which were carried out at conversions of DMDS lying between 35 and 45%.

TABLE 2

| CATALYST | | CONVERSION (%) | RELATIVE SELECTIVITIES (%) | |
| --- | --- | --- | --- | --- |
| Metal | Mass (g) | DMDS | MeSH | DMS |
| none | 0.117 | 44 | 21 | 79 |
| Mo | 0.077 | 37 | 19.6 | 80.4 |
| Ni | 0.061 | 36 | 11.5 | 88.5 |
| Co | 0.050 | 41 | 13.4 | 86.6 |
| NiMo | 0.118 | 45 | 55.3 | 44.7 |
| CoMo | 0.076 | 38 | 31.1 | 68.9 |
| NiW | 0.119 | 35 | 55.5 | 44.5 | c) Hydrogenation of dimethyl disulphide in the presence of hydrogen sulphide

The only modification to the experimental procedure of Example 1b was the addition of 0.1 mol of hydrogen sulphide per mole of DMDS. Table 3 which follows summarizes the results obtained under these conditions and at a temperature of 200° C.

TABLE 3

| CATALYST | | CONVERSION (%) | RELATIVE SELECTIVITIES (%) | |
|---|---|---|---|---|
| Metal | Mass (g) | DMDS | MeSH | DMS |
| none | 0.120 | 51 | 73 | 27 |
| Mo | 0.080 | 19 | 100 | 0 |
| Ni | 0.060 | 14 | 85 | 15 |
| NiMo | 0.105 | 32 | 99 | 1 | d) Hydrogenation of dimethyl disulphide in the presence of water

The only modification made to the experimental procedure of Example 1b was the addition of 0.1 mol of water per mole of DMDS. The results which were obtained under these conditions and at a temperature of 200° C. are presented in Table 4.

TABLE 4

| CATALYST | | CONVERSION (%) | RELATIVE SELECTIVITIES (%) | |
|---|---|---|---|---|
| Metal | Mass (g) | DMDS | MeSH | DMS |
| NiMo | 0.118 | 41 | 100 | 0 |
| CoMo | 0.076 | 11 | 100 | 0 |
| NiW | 0.119 | 27 | 100 | 0 |

Complementary tests in the presence of water were performed with the catalyst which gave the best results (Ni—Mo/alumina).

The results summarized in Table 5 were obtained by working at various degrees of conversion of DMDS by varying the mass of catalyst. Even at high conversion (91%), the selectivity towards methyl mercaptan remained at a high level (95.6%).

TABLE 5

| Conversion of DMDS (%) | 29 | 40 | 58 | 79.2 | 91 |
|---|---|---|---|---|---|
| MeSH Selectivity (%) | 100 | 100 | 98 | 97 | 95.6 |

The results summarized in Table 6 were obtained by varying the proportion of water added. It is observed that neither the conversion nor the selectivity were modified by increasing the proportion of water.

TABLE 6

| $H_2O$/DMDS Molar ratio | 0.13 | 0.27 | 0.40 | 0.67 | 1.20 |
|---|---|---|---|---|---|
| Conversion of DMDS (%) | 42 | 42 | 41 | 39 | 39 |
| MeSH Selectivity (%) | 100 | 100 | 100 | 100 | 100 |

EXAMPLE 2

The hydrogenolysis tests on DMDS in the presence of water reported in this example were performed using the same commercial Ni—Mo/alumina catalyst as in Example 1 (catalyst HR 346 from PROCATALYSE).

Sulphuration of the Ni—Mo/alumina catalyst (50 g) was effected directly in the reactor used for carrying out the hydrogenolysis of the DMDS, by treatment at 400° C. for 4 hours using a hydrogen sulphide/hydrogen mixture (containing 15 mol % of $H_2S$) at an hourly flow rate of 2 liters of mixture per gram of catalyst.

The hydrogenolysis tests were performed at atmospheric pressure in a stainless steel tubular reactor (internal diameter: 25 mm) fitted with a sleeve for measuring the temperature and housed at the center of an electric oven with three independent heating zones. The DMDS and water, injected at controlled flow rates in liquid form, and the gaseous hydrogen were introduced into the upper part of the reactor, which served as a preheating zone.

The reaction effluents were maintained as gases by heating the circulation lines outside the reactor and were sent to an injection valve coupled to a chromatograph which analyzed these effluents directly.

Table 7 which follows summarizes the results obtained by varying the temperature (150°, 175° and 200° C.) and the hourly flow rate of DMDS (42 to 166 g/h), but by keeping the $H_2$/DMDS and DMDS/$H_2O$ molar ratios constant at 2.1 and 2.7 respectively.

TABLE 7

| TEMPERATURE (°C.) | DMDS g/h | CONVERSION OF DMDS (%) | SELECTIVITY TOWARDS MeSH (%) |
|---|---|---|---|
| 150 | 63 | 71.8 | >99.5 |
| 150 | 125 | 60 | >99.5 |
| 175 | 63 | 100 | >99.5 |
| 175 | 83 | 92.2 | >99.5 |
| 175 | 104 | 91 | >99.5 |
| 175 | 166 | 87.6 | >99.5 |
| 200 | 42 | 100 | ≧99.5 |
| 200 | 63 | 100 | ≧99.5 |
| 200 | 104 | 98.4 | ≧99.5 |
| 200 | 125 | 93.2 | ≧99.5 |

Table 8 which follows summarizes the results obtained at 175° C. by varying the proportion of hydrogen for the same flow rate of DMDS (166 g/h) and a DMDS/$H_2O$ molar ratio kept constant at 2.7.

TABLE 8

| $H_2$/DMDS MOLAR RATIO | CONVERSION OF DMDS (%) | SELECTIVITY TOWARDS MeSH (%) |
|---|---|---|
| 1.2 | 65.3 | >99.5 |
| 1.4 | 72.5 | >99.5 |
| 1.7 | 80.0 | >99.5 |
| 2.1 | 87.6 | >99.5 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the selective preparation of methyl mercaptan by catalytic hydrogenation of dimethyl disulphide on a catalyst based on sulphide(s) of at least one transition metal, comprising performing the process in the presence of water and/or hydrogen sulphide.

2. Process according to claim 1, wherein the proportion of water or of hydrogen sulphide ranges from 0.01 to 50% by weight relative to the dimethyl disulphide.

3. Process according to claim 1, wherein the hydrogen/dimethyl disulphide molar ratio is between 0.1 and 50.

4. Process according to claim 1, wherein the process is performed at a temperature ranging from 50° to 400° C.

5. Process according to claim 1, wherein the process is performed at between atmospheric pressure up to 50 bar.

6. Process according to claim 1, wherein the catalyst is based on sulphide(s) of nickel, cobalt, molybdenum and/or tungsten.

7. Process according to claim 1, wherein the catalyst consists of nickel and molybdenum sulphides on an alumina support.

8. Process according to claim 2, wherein the range is between 0.1 and 15%.

9. Process according to claim 3, wherein the molar ratio is between 0.5 and 10.

10. Process according to claim 3, wherein the molar ratio is between 0.8 and 4.

11. Process according to claim 4, wherein the temperature ranges between 100° and 250° C.

12. Process for the selective preparation of methyl mercaptan by catalytic hydrogenation of dimethyl disulphide on a catalyst based on sulphide(s) of at least one transition metal selected from nickel, cobalt, molybdenum and/or tungsten comprising performing the process in the presence of water, wherein the proportion of water ranges from 0.01 to 50% by weight relative to the dimethyl disulphide.

13. The process of claim 12, wherein said catalyst consists of nickel and molybdenum sulphides on an alumina support.

* * * * *